(12) United States Patent
Deshpande

(10) Patent No.: US 8,450,398 B2
(45) Date of Patent: May 28, 2013

(54) OXYGEN SCAVENGERS, COMPOSITIONS COMPRISING THE SCAVENGERS, AND ARTICLES MADE FROM THE COMPOSITIONS

(75) Inventor: Girish N. Deshpande, Bolingbrook, IL (US)

(73) Assignee: Constar International, Inc., Philadelphia, PA (US)

( * ) Notice: Subject to any disclaimer, the term of this patent is extended or adjusted under 35 U.S.C. 154(b) by 100 days.

(21) Appl. No.: 12/945,355

(22) Filed: Nov. 12, 2010

(65) Prior Publication Data

US 2011/0117301 A1  May 19, 2011

Related U.S. Application Data

(60) Provisional application No. 61/261,219, filed on Nov. 13, 2009.

(51) Int. Cl.
*C07D 209/48* (2006.01)

(52) U.S. Cl.
USPC .............. 524/94; 524/401; 524/435; 524/56; 524/57; 524/104; 525/437; 544/1; 548/577

(58) Field of Classification Search
USPC ........ 524/401, 435, 86, 87, 94, 104; 525/437; 544/577; 548/1
See application file for complete search history.

(56) References Cited

U.S. PATENT DOCUMENTS

| | | | |
|---|---|---|---|
| 4,536,409 A | 8/1985 | Farrell et al. | |
| 4,786,671 A | 11/1988 | Kress et al. | |
| 5,021,515 A | 6/1991 | Cochran et al. | |
| 5,049,624 A | 9/1991 | Adams et al. | |
| 5,075,362 A | 12/1991 | Hofeldt et al. | |
| 5,211,875 A | 5/1993 | Speer et al. | |
| 5,250,592 A * | 10/1993 | Nesvadba | 524/89 |
| 5,639,815 A | 6/1997 | Cochran et al. | |
| 5,955,527 A | 9/1999 | Cochran et al. | |
| 6,610,234 B2 | 8/2003 | Akkapeddi et al. | |
| 6,780,916 B2 | 8/2004 | Tung et al. | |
| 7,879,930 B2 | 2/2011 | Liu | |
| 2006/0180790 A1 | 8/2006 | Deshpande et al. | |
| 2006/0182911 A1 | 8/2006 | Tammaji et al. | |
| 2006/0247388 A1 | 11/2006 | Hale et al. | |
| 2007/0066731 A1 | 3/2007 | Tattum et al. | |
| 2007/0241309 A1 | 10/2007 | Uradnisheck | |
| 2008/0161472 A1 | 7/2008 | Jenkins et al. | |
| 2008/0255280 A1 | 10/2008 | Sims et al. | |
| 2008/0277622 A1* | 11/2008 | Deshpande et al. | 252/188.28 |
| 2009/0030115 A1 | 1/2009 | Liu | |
| 2009/0278087 A1 | 11/2009 | Deshpande et al. | |

FOREIGN PATENT DOCUMENTS

| | | |
|---|---|---|
| EP | 0144 807 A2 | 6/1985 |
| WO | WO-95/02616 A2 | 1/1995 |
| WO | WO-2006/088889 A2 | 8/2006 |
| WO | WO-2009/152114 A1 | 12/2009 |

OTHER PUBLICATIONS

Grawe, T., et al; Journal of Organic Chemistry, 2002, vol. 67, p. 3755-3763.*
Vacca, A., et al; Journal of the American Chemical Society, 2004, vol. 126, p. 16456-16465.*
Bandi, S. et al., "The mechanism of color generation in poly(ethylene terephthalate) / polyamide blends," Polymer Degradation and Stability, 2005, 88: pp. 341-348.
Grawe, T. et al., "Self-Assembly of Ball-Shaped Molecular Complexes in Water," Journal of Organic Chemistry, 2002, vol. 67(11): pp. 3755-3763.
Vacca, a. et al., "A New Tripodal Receptor for Molecular Recognition of Monosaccharides. A Paradigm for Assessing Glycoside Binding Affinities and Selectivities by 1H NMR Spectroscopy," Journal of the American Chemical Society, 2004, vol. 126(50): pp. 16456-16465.
International Search Report with Written Opinion issued on Oct. 29, 2008 for Intl. App. No. PCT/US2008/063250, filed May 9, 2008 (Inventor—G. Deshpande et al.; Applicant—Constar International, Inc.; pp. 1-14).
International Preliminary Report on Patentability issued on Nov. 10, 2009 for Intl. App. No. PCT/US2008/063250, filed May 9, 2008 (Inventor—G. Deshpande et al.; Applicant—Constar International, Inc.; pp. 1-7).
International Search Report with Written Opinion issued on Jun. 27, 2011 for Intl. App. No. PCT/US2010/050719, Sep. 29, 2010 (Inventor—G. Deshpande; Applicant—Constar International, Inc.; pp. 1-7).
International Search Report with Written Opinion issued on Jul. 28, 2011 for Intl. App. No. PCT/US2010/056594, Nov. 12, 2010 (Inventor—G. Deshpande; Applicant—Constar International, Inc.; pp. 1-8).
International Search Report with Written Opinion issued on Aug. 2, 2011 for Intl. App. No. PCT/US2010/056598, Nov. 12, 2010 (Inventor—G. Deshpande; Applicant—Constar International, Inc.; pp. 1-13).
International Search Report with Written Opinion issued on Jul. 25, 2011 for Intl. App. No. PCT/US2010/056585, Nov. 12, 2010 (Inventor—G. Deshpande; Applicant—Constar International, Inc.; pp. 1-8).
First Office Action issued on Jul. 6, 2011 for CN Pat. App. No. 200880023116.X, which is national phase of Intl. App. No. PCT/US2008/063250, filed May 9, 2008 (Inventor—G. Deshpande et al.; Applicant—Constar International, Inc.; pp. 1-7).
Preliminary Amendment filed on Dec. 10, 2009 for EP Pat. App. No. 08795847.6, which is national phase of Intl. App. No. PCT/US2008/063250, filed May 9, 2008 (Inventor—G. Deshpande et al.; Applicant—Constar International, Inc.; pp. 1-5).

(Continued)

*Primary Examiner* — Robert Jones, Jr.
(74) *Attorney, Agent, or Firm* — Ballard Spahr LLP

(57) ABSTRACT

The disclosure relates to oxygen scavenging molecules, compositions, methods of making the compositions, articles prepared from the compositions, and methods of making the articles. This abstract is intended as a scanning tool for purposes of searching in the particular art and is not intended to be limiting of the present invention.

14 Claims, 2 Drawing Sheets

OTHER PUBLICATIONS

Office Action issued on Sep. 23, 2011 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-3).

Notice of Allowance issued on Jun. 24, 2011 for U.S. Appl. No. 12/117,849, filed May 9, 2008 (Inventor—G. Deshpande et al.; Applicant—Constar International, Inc.; pp. 1-7).

Response after Non-Final Office Action filed on Apr. 8, 2011 for U.S. Appl. No. 12/117,849, filed May 9, 2008 (Inventor—G. Deshpande et al.; Applicant—Constar International, Inc.; pp. 1- 16).

Non-Final Office Action issued on Jan. 20, 2011 for U.S. Appl. No. 12/117,849, filed May 9, 2008 (Inventor—G. Deshpande et al.; Applicant—Constar International, Inc.; pp. 1-5).

Response to Election/Restriction Requirement filed on Dec. 17, 2010 for U.S. Appl. No. 12/117,849, filed May 9, 2008 (Inventor—G. Deshpande et al.; Applicant—Constar International, Inc.; pp. 1-3).

Requirement for Restriction/Election issued on Oct. 5, 2010 for U.S. Appl. No. 12/117,849, filed May 9, 2008 (Inventor—G. Deshpande et al.; Applicant—Constar International, Inc.; pp. 1-5).

Office Action issued on Sep. 30, 2011 for CL Pat. App. No. 1391-08, national phase of Intl. App. No. PCT/US2008/063250, filed May 9, 2008 (Inventor—G. Deshpande et al.; Applicant—Constar International, Inc.; pp. 1-21).

Response to Office Action filed on Mar. 27, 2012 for CL Pat. App. No. 1391/2008, national phase of Intl. App. No. PCT/US2008/063250, filed May 9, 2008 (Inventor—G. Deshpande et al.; Applicant—Constar International, Inc.; pp. 1-21).

Response to Office Action filed on Feb. 3, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-4).

Second Office Action issued on Mar. 16, 2012 for CN Pat. App. No. 200880023116.X, national phase of Intl. App. No. PCT/US2008/063250, filed May 9, 2008 (Inventor—G. Deshpande et al.; Applicant—Constar International, Inc.; pp. 1-11).

Response to Office Action filed on Aug. 20, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-2).

Notice of Allowance issued on Dec. 23, 2011 for U.S. Appl. No. 13/164,477, filed Jun. 20, 2011 (Inventor—G. Deshpande et al.; Applicant—Constar International, Inc.; pp. 1-8).

International Preliminary Report on Patentability issued on Apr. 12, 2012 for Intl. App. No. PCT/US2010/050719, Sep. 29, 2010 (Inventor—G. Deshpande; Applicant—Constar International, Inc.; pp. 1-5).

International Preliminary Report on Patentability issued on May 24, 2012 for Intl. App. No. PCT/US2010/056594, Nov. 12, 2010 (Inventor—G. Deshpande; Applicant—Constar International, Inc.; pp. 1-5).

International Preliminary Report on Patentability issued on May 24, 2012 for Intl. App. No. PCT/US2010/056585, Nov. 12, 2010 (Inventor—G. Deshpande; Applicant—Constar International, Inc.; pp. 1-6).

International Preliminary Report on Patentability issued on May 24, 2012 for Intl. App. No. PCT/US2010/056598, Nov. 12, 2010 (Inventor—G. Deshpande; Applicant—Constar International, Inc.; pp. 1-7).

Requirement for Restriction/Election issued on Jun. 12, 2012 for U.S. Appl. No. 12/945,351, filed Nov. 12, 2010 (Inventor—G. Deshpande et al.; Applicant—Constar International, Inc.; pp. 1-10).

Requirement for Restriction/Election issued on May 9, 2012 for U.S. Appl. No. 12/893,817, filed Sep. 29, 2010 (Inventor—G. Deshpande et al.; Applicant—Constar International, Inc.; pp. 1-8).

Response to Election/Restriction Requirement filed on Aug. 10, 2012 for U.S. Appl. No. 12/893,817, filed Sep. 29, 2010 (Inventor—G. Deshpande et al.; Applicant—Constar International, Inc.; pp. 1-2).

Office Action issued on Apr. 19, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-2).

Examination Report issued for AU Pat. App. No. 2008251476, national phase of Intl. App. No. PCT/US2008/063250, filed May 9, 2008 (Inventor—G. Deshpande et al.; Applicant—Constar International, Inc.; pp. 1-3).

Preliminary Amendment filed on Nov. 21, 2012 for EP Pat. App. No. 10822439.5, national phase of Intl. App. No. PCT/US2010/050719, Sep. 29, 2010 (Inventor—G. Deshpande; Applicant—Constar International, Inc.; pp. 1-15).

Response to Requirement for Restriction/Election filed on Oct. 12, 2012 for U.S. Appl. No. 12/945,351, filed Nov. 12, 2010 (Inventor—G. Deshpande et al.; Applicant—Constar International, Inc.; pp. 1-3).

Requirement for Restriction/Election issued on Nov. 2, 2012 for U.S. Appl. No. 12/945,353, filed Nov. 12, 2010 (Inventor—G. Deshpande et al.; Applicant—Constar International, Inc.; pp. 1-10).

Chen et al, "Efficient enhancement of DNA cleavage activity by introducing guanidinium groups into diiron(III) complex", Bioorganic & Medicinal Chemistry Letters, Pergamon, Elsevier Science, GB, vol. 18, No. 1, Nov. 5, 2007, pp. 109-113.

Ragusa, A. et al, "Novel Enantioselective Receptors for N-Protected; Glutamate and Aspartate", Chemistry—A European Journal, vol. 11, No. 19, Sep. 19, 2005, pp. 5674-5688.

Zhan-Ting, L. et al., "The synthesis of fluorine-containing azamacrocyclic; compounds", Heterocycles.International Journal for Reviews and Communications in Heterocyclic Chemistry, Elsevier Science Publishers B.V. Amsterdam, NL, vol. 34, No. 9, Jan. 1, 1992, pp. 1729-1736.

Rossi, S. et al., "A Highly Enantioselective Receptor for N-Protected Glutamate and Anomalous Solvent-Dependent Binding Properties", Angew. Chem. Int. Ed., vol. 41, No. 22, 2002, pp. 4233-4236.

Extended European Search Report issued on Mar. 9, 2013 for EP Pat. App. No. 10830816.4, national phase of Intl. App. No. PCT/US2010/056585, Nov. 12, 2010 (Inventor—G. Deshpande; Applicant—Constar International, Inc.; pp. 1-7).

Non Final Office Action issued on Feb. 14, 2013 for U.S. Appl. No. 12/893,817, filed Sep. 29, 2010 (Inventor—G. Deshpande et al.; Applicant—Constar International, Inc.; pp. 1-8).

* cited by examiner

OXYGEN SCAVENGERS, COMPOSITIONS COMPRISING THE SCAVENGERS, AND ARTICLES MADE FROM THE COMPOSITIONS

CROSS-REFERENCE TO RELATED APPLICATIONS

This application claims the benefit of and priority to U.S. provisional patent application Ser. No. 61/261,219 filed Nov. 13, 2009, the entire disclosure of which is incorporated by reference herein.

BACKGROUND

Many polymers used in packaging materials and other articles are permeable to oxygen. When oxygen permeates a polymeric composition or article, it can cause oxidative damage to the contents of the package. It is therefore desirable for certain polymer compositions and articles to have oxygen scavenging capability, such that when oxygen permeates the composition or article, oxidative damage can be mitigated.

It is known in the art to include an oxygen scavenger in the packaging structure for the protection of oxygen sensitive materials. Such scavengers are believed to react with oxygen that is trapped in the package or that permeates from outside of the package, thus extending to life of package contents. These packages include films, bottles, containers, and the like. Food, beverages (such as beer and fruit juices), cosmetics, medicines, and the like are particularly sensitive to oxygen exposure and require high barrier properties to oxygen to preserve the freshness of the package contents and avoid changes in flavor, texture and color.

Therefore, a need exists for compounds and compositions having improved oxygen scavenging capacity. These needs and other needs are satisfied by the present invention.

SUMMARY

In accordance with the purpose(s) of the invention, as embodied and broadly described herein, the invention, in one aspect, relates to oxygen scavenging molecules, compositions comprising the molecules, and articles prepared from the compositions.

Also disclosed are polymer compositions comprising the disclosed oxygen scavenging molecules.

Also disclosed are articles prepared from the disclosed polymers and compositions.

Also disclosed are methods of making oxygen scavenging molecules and polymer compositions comprising the disclosed oxygen scavenging molecules.

Also disclosed are the products of the disclosed methods.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Figure 1:
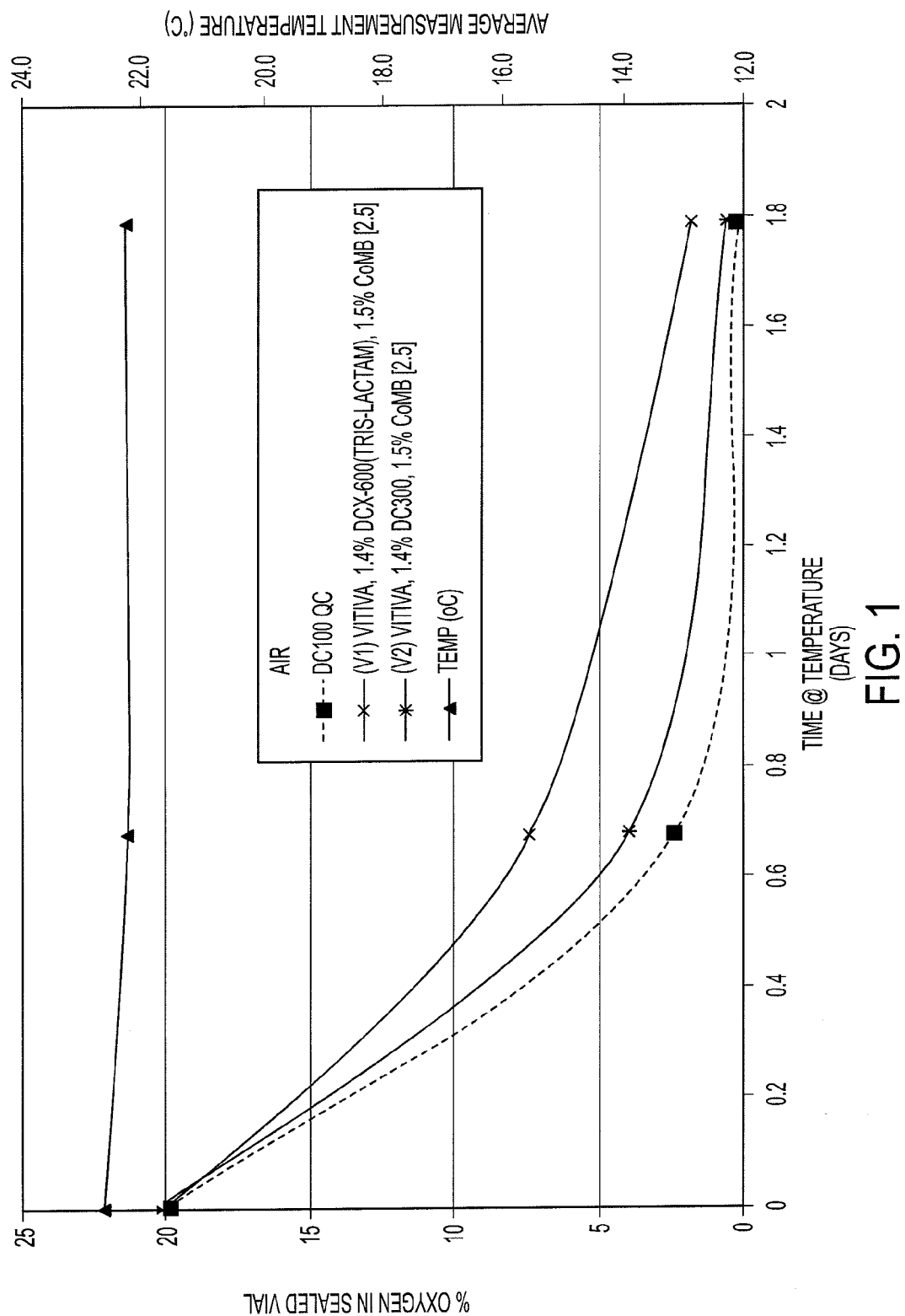
FIG. 1 shows Oxysense™ $O_2$ scavenging data for DCX-600 (hexa-functional scavenger) and DC-300 (tetra-functional scavenger) containing plaques, as described in Example 2.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where said event or circumstance occurs and instances where it does not.

As used herein, the term "substantially" means that the subsequently described event or circumstance completely occurs or that the subsequently described event or circumstance generally, typically, or approximately occurs. For example, when the specification discloses that substantially all of an agent is released, a person skilled in the relevant art would readily understand that the agent need not be completely released. Rather, this term conveys to a person skilled in the relevant art that the agent need only be released to an extent that an effective amount is no longer unreleased.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or from two to four. In one aspect, a collection of oligomers can have an average number of repeating units of from about two to about ten, for example, from about two to about eight, from about two to about six, or from about two to about four.

As used herein, the term "star polymer" refers to a branched polymer molecule in which a single branch point gives rise to multiple linear chains or arms. The single branch point can be a single chemical moiety or can be a highly crosslinked section of polymer. In one aspect, a star polymer can be generally spherical in shape. In a further aspect, a star polymer can be particle shaped. If the arms are identical the star polymer molecule is said to be regular. If adjacent arms are composed of different repeating subunits, the star polymer molecule is said to be variegated.

As used herein, the term "molecular weight" (MW) refers to the mass of one molecule of that substance, relative to the unified atomic mass unit u (equal to 1/12 the mass of one atom of carbon-12).

As used herein, the term "number average molecular weight" ($M_n$) refers to the common, mean, average of the molecular weights of the individual polymers. $M_n$ can be determined by measuring the molecular weight of n polymer molecules, summing the weights, and dividing by n. $M_n$ is calculated by:

$$\overline{M}_n = \frac{\sum_i N_i M_i}{\sum_i N_i},$$

wherein $N_i$ is the number of molecules of molecular weight $M_i$. The number average molecular weight of a polymer can be determined by gel permeation chromatography, viscometry (Mark-Houwink equation), light scattering, analytical ultracentrifugation, vapor pressure osmometry, end-group titration, and colligative properties.

As used herein, the term "weight average molecular weight" ($M_W$) refers to an alternative measure of the molecular weight of a polymer. $M_W$ is calculated by:

$$\overline{M}_w = \frac{\sum_i N_i M_i^2}{\sum_i N_i M_i},$$

wherein $N_i$ is the number of molecules of molecular weight $M_i$. Intuitively, if the weight average molecular weight is w, and a random monomer is selected, then the polymer it belongs to will have a weight of w on average. The weight average molecular weight can be determined by light scattering, small angle neutron scattering (SANS), X-ray scattering, and sedimentation velocity.

As used herein, the terms "polydispersity" and "polydispersity index" (PDI) refer to the ratio of the weight average to the number average ($M_W/M_n$).

As used herein, the term "compatibilizing agent" refers to a small molecule or polymer that has both polar and non-polar functional groups. For example, a fatty-acid ester has both polar and non-polar functional groups.

A weight percent (wt. %) of a component, unless specifically stated to the contrary, is based on the total weight of the formulation or composition in which the component is included.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

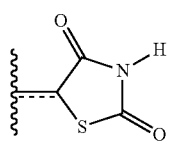

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

In some aspects, a structure of a compound can be represented by a formula:

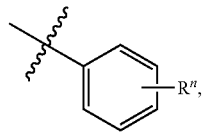

which is understood to be equivalent to a formula:

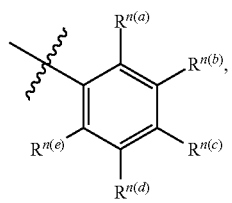

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of from 1 to 24 carbon atoms, for example from 1 to 12 carbons, from 1 to 8 carbons, from 1 to 6 carbons, or from 1 to 4 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$— where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1$C(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "thiol" as used herein is represented by the formula —SH.

Certain instances of the above defined terms may occur more than once in the structural formulae, and upon such occurrence each term shall be defined independently of the other.

As used herein, the term "effective amount" refers to an amount that is sufficient to achieve the desired result or to have an effect on an undesired condition. For example, a "visually effective amount" refers to an amount that is sufficient to achieve the desired result (i.e., impart color to a composition or an article), but is generally insufficient to cause adverse side affects (e.g., warping of a polymeric article).

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The disclosed compounds are N-allylic amide compounds or N-benzylic amide compounds. The amide compound is useful as an oxygen scavenger. The oxygen scavenging ability of the amide compound can be enhanced, in various aspects, by the presence of a transition metal.

The disclosed N-allylic or N-benzylic amide compounds have the general structure shown below:

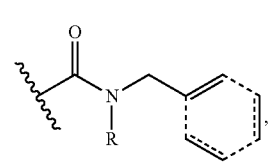

wherein each --- independently denotes an optional covalent bond.

The N-allylic or N-benzylic amide compound can be further substituted and more than one amide functionality can be present in a compound. In one aspect, an N-allylic or N-benzylic amide compound can be polymeric. In a further aspect, an N-allylic or N-benzylic amide compound can be nonpolymeric.

In one aspect, the amide compound has a structure of Formula I or II:

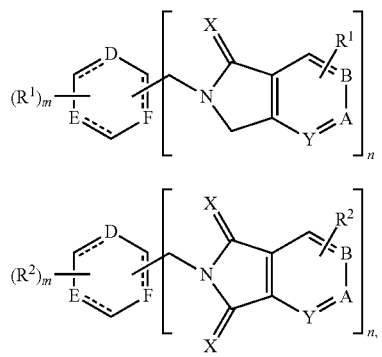

wherein the symbol --- when used in conjunction with a bond line represents a single or a double bond; wherein n is 3, 4, 5, or 6; wherein m is an integer from 0 to 6-n; wherein each X is independently selected from the group consisting of O, S, and NH; wherein each Y, each A, and each B are independently selected from the group consisting of N, $CR^1$, and $CR^2$; wherein D, E, and F are independently selected from the group consisting of CH, N, O, and S; and wherein each $R^1$ and each $R^2$ is independently selected from the group consisting of H, alkyl, aryl, electron withdrawing groups, electron releasing groups, and a transition metal.

In one aspect, the compound of formula I or II can be represented by the following formula:

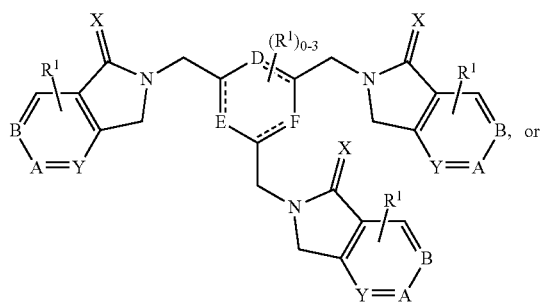

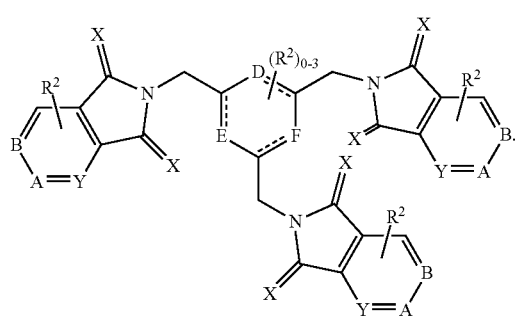

In a further aspect, the compound has a structure of Formula III or Formula IV:

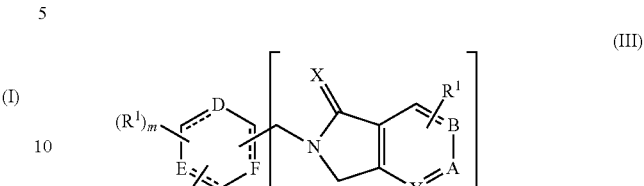

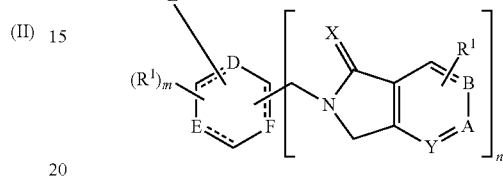

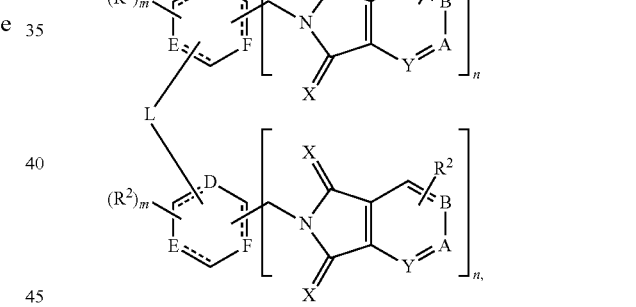

wherein the symbol --- when used in conjunction with a bond line represents a single or a double bond; wherein each n is independently 1-5; wherein m is an integer from 0 to 5-n; wherein each X is independently selected from the group consisting of O, S, and NH; wherein each Y, each A, and each B are independently selected from the group consisting of N, $CR^1$, and $CR^2$; wherein D, E, and F are independently selected from the group consisting of CH, N, O, and S; wherein each $R^1$ and each $R^2$ is independently selected from the group consisting of H, alkyl, aryl, electron withdrawing groups, electron releasing groups, and a transition metal; and wherein L is a divalent linking group selected from C2-C12 aliphatic or cyclic ether, C2-C12 aliphatic or cyclic amide, C6 to C12 aromatic amide, C2-C12 aliphatic or cyclic amine, C6-C12 aromatic amine, C2-C12 aliphatic or cyclic ester and C6 to C12 aromatic ester.

In a further aspect, the compound has a structure of Formula V or Formula VI:

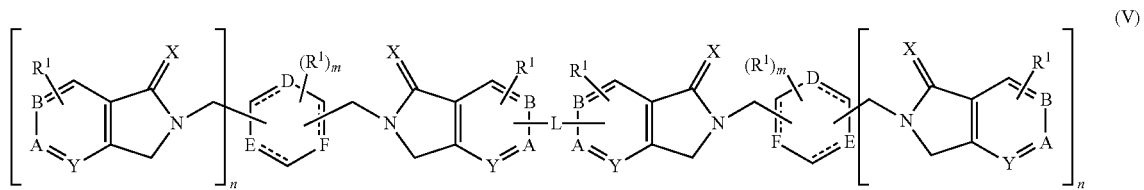

(V)

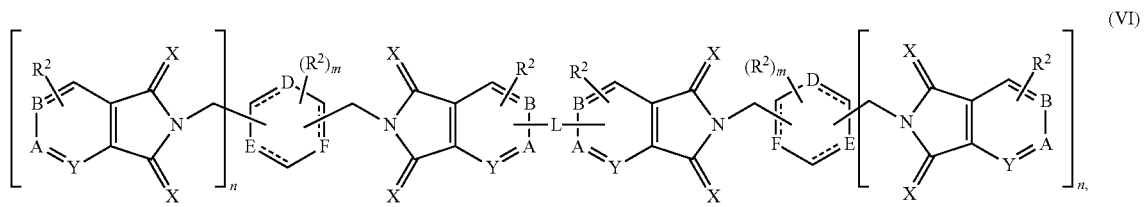

(VI)

wherein the symbol --- when used in conjunction with a bond line represents a single or a double bond; wherein each n is independently 0-5; wherein m is an integer from 0 to 5-n; wherein each X is independently selected from the group consisting of O, S, and NH; wherein each Y, each A, and each B are independently selected from the group consisting of N, $CR^1$, and $CR^2$; wherein D, E, and F are independently selected from the group consisting of CH, N, O, and S; wherein each $R^1$ and each $R^2$ is independently selected from the group consisting of H, alkyl, aryl, electron withdrawing groups, electron releasing groups, and a transition metal; and wherein L is a divalent linking group selected from C2-C12 aliphatic or cyclic ether, C2-C12 aliphatic or cyclic amide, C6 to C12 aromatic amide, C2-C12 aliphatic or cyclic amine, C6-C12 aromatic amine, C2-C12 aliphatic or cyclic ester and C6 to C12 aromatic ester.

Generally, linking group L is a divalent organic residue. Suitable linking groups L include divalent aliphatic chains, divalent aliphatic or cyclic ethers, divalent aliphatic or cyclic amides, divalent aromatic amide, divalent aliphatic or cyclic amines, divalent aromatic amines, divalent aliphatic or cyclic esters and divalent aromatic esters, such as those exemplified in Table 1 below. As used in the table below, the term "tether compound" refers to a difunctional organic compound capable of reactions with ring substitutents of disclosed moieties to form covalent bonds, thereby chemically connecting the ring substitutents via a divalent organic residue of the tether compound, referred to as a linking group, L. Examples of tether compounds include dielectrophilic compounds (e.g., diacyl halides, cyclic anhydrides, and bis-alkyl halides) for linking nucleophilic ring substituents (e.g., hydroxides, thiols, and amines). Further examples of tether compounds include dinucleophilic compounds (e.g., bis-hydroxides, bis-thiols, and bis-amines) for linking electrophilic ring substituents (e.g., acyl halides and alkyl halides). Selected examples are illustrated structurally in Table 1.

TABLE 1

| L | Ring Substituent | Tether Compound |
|---|---|---|
| [O-C(=O)-R-C(=O)-O] | [O-H] | [Z-C(=O)-R-C(=O)-Z], wherein Z is OH, OR', halogen, or psuedohalogen; or [oxetane-2,4-dione with R] |
| [S-C(=O)-R-C(=O)-S] | [S-H] | |
| [N(R')-C(=O)-R-C(=O)-N(R')] | [N(R')-H] | |

TABLE 1-continued

| L | Ring Substituent | Tether Compound |
|---|---|---|
| (ester-R-ester) | (acyl-Z) | HO-R-OH |
| (thioester-R-thioester) | | HS-R-SH |
| (amide-R-amide with R') | | HN(R')-R-N(R')H |
| (ether-CH2-R-CH2-ether) | (ether-H) | Z-CH2-R-CH2-Z, wherein each Z is OH, OR', halogen, or psuedohalogen. |
| (thioether-CH2-R-CH2-thioether) | (thioether-H) | |
| (amine-CH2-R-CH2-amine with R') | (amine-H with R') | |
| (ether-CH2-R-CH2-ether) | (C-Z) | HO-CH2-R-CH2-OH |
| (thioether-CH2-R-CH2-thioether) | | HS-CH2-R-CH2-SH |
| (amine-CH2-R-CH2-amine with R') | | HN(R')-CH2-R-CH2-N(R')H |

In Table 1, R is an optionally substituted divalent organic residue; for example, R can be selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl. In further aspects, R can be linear, cyclic, or branched. Typically, R has from 1 to 48 carbons, from 1 to 24 carbons, from 1 to 12 carbons, from 1 to 8 carbons, from 1 to 6 carbon, or from 1 to 4 carbons.

In further aspects, R' is an optionally substituted organic residue. Typically, R' has from 1 to 12 carbons, from 1 to 8 carbons, from 1 to 6 carbon, or from 1 to 4 carbons. For example, R' can be methyl, ethyl, propyl, butyl, pentyl, or hexyl.

It is also contemplated that the functional groups selected for use in fabricating L can be used in combinations other than those shown in the Table. For example, in a further aspect, L can be:

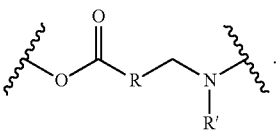

Linking groups L can be readily prepared by methods known to those of skill in the art of organic synthesis.

The alkyl group of the compound of Formulae (I-VI) can be a branched or unbranched saturated hydrocarbon group of 1 to 24 carbon atoms, e.g. 1 to 18 carbons atoms, 1 to 14 carbon atoms, 1 to 12 carbon atoms, 1 to 10 carbon atoms, 1 to 8, 1 to 6 carbon atoms, or 1 to 4 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. The alkyl group can be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol, as described below. The alkyl group can be halogenated, which includes an alkyl group that is substituted with one or more halide, e.g., fluorine, chlorine, bromine, or iodine. The alkyl group can also be a lower alkyl group, which is an alkyl group containing from one to six (e.g., from one to four) carbon atoms.

The aryl group of the compound of Formulae (I-VI) can be any carbon-based aromatic group including but not limited to, benzene, naphthalene, phenyl, biphenyl, etc. The aryl group can also be heteroaryl, which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein. A biaryl group is a specific type of aryl group and is included in the definition of aryl. Biaryl refers to two aryl groups that are bound together via a fused ring structure, as in naphthalene, or are attached via one or more carbon-carbon bonds, as in biphenyl.

Suitable electron withdrawing groups and electron releasing groups are generally known in the art. Preferred electron withdrawing groups include nitro, carboxylic acid, esters, for example loweralkyl esters, and cyano. Preferred electron releasing groups include branched and straight chain alkyl groups, for example, methyl, ethyl, propyl, isopropyl, butyl, isobutyl, and tert-butyl. Other preferred electron releasing groups include alkoxy, for example methoxy and ethoxy. Other preferred electron releasing groups include thioalkyl. Still other preferred electron releasing groups include amines, for example —$NH_2$, and NH(loweralkyl), and N(loweralkyl)$_2$.

Oxygen scavenging amide compounds are disclosed in U.S. Patent Application Publication No. 20080277622, Deshpande et al. "Oxygen Scavenging Molecules, Articles Containing Same, And Methods of Their Use," which is incorporated herein by this reference for its teaching of amide compounds, their preparation, and their use as oxygen scavenging materials.

One version of Compound I can be prepared by reacting one mole of 1,3,5-trimethylaminobenzene with three moles of 1-isoindolinone (CAS # 87-41-2) in a continuous stirred tank reactor (CSTR) using a solvent such as xylene under N2 pressure and at temperatures exceeding 200° C. After distilling off water as a byproduct of the reaction, the reaction product is isolated and purified using successive solvent washes.

One version of Compound II can be prepared by reacting one mole of 1,3,5-trimethylaminobenzene with three moles of phthalic anhydride under similar reaction and purification conditions described above.

One version of Compound V with an ester linking group L can be prepared by reaction of 2 moles of meta-xylene bis(5-carboxylsoindolin-1-one) with one mole of a diol in an acidic environment to yield a structure similar to that described in Compound V. It is possible to use aliphatic diols such as ethylene glycol or cyclic diols such as 1,4-cyclohexanediol or aromatic diols such as benzene-1,4-diol as linking groups One version of Compound V with an amide linking group L can be prepared by reaction of 2 moles of meta-xylene bis(5-carboxylsoindolin-1-one) with one more of a diamine to yield a structure similar to that described in Compound V. It is possible to use aliphatic diamines such as ethylene diamine or cyclic diamines such as 1,4-cyclohexanediamine or aromatic diamines such as 1,4-phenylenediamine One version of Compound V with an ether linking group can be prepared by the reaction of 2 moles of meta-xylene bis(5-hydroxylisoindolin-1-one) with one mole of 1,2-dichloroethane to yield a structure similar to that described by compound V. Alternatively, one can use 2 moles of meta-xylene bis(5-chloroisoindolin-1-one) to react with itself in presence of sodium benzoate (or any sodium salt of organic acid) and heat to give an ether linking group, similar to that described in Compound V. It is possible to use aliphatic dichloro compounds or cyclic dichloro compounds or aromatic dichloro compounds to obtain a range of ether based linking groups.

One version of Compound V with amine based linking group can be prepared by reaction of one mole of meta-xylene bis(5-chloroisoindolin-1-one) with one mole of meta-xylene bis(5-aminoisoindolin-1-one) in an basic medium with heat to yield Compound V with an amine based linking group. Another version of Compound V with an amine based linking group can be prepared by reaction of 2 moles of meta-xylene bis(5-chloroisoindolin-1-one) with one mole of ethylene diamine in a basic medium to yield a amine linked Compound V. It is possible to use aliphatic diamino compounds or cyclic diamino compounds or aromatic diamino compounds to obtain a range of amine based linking groups.

The amide compound can in certain aspects be complexed to a transition metal. For example, the amide compound can be complexed to the transition metal through one or more aryl groups, for example through pi-cloud complexation. The amide compound can also be polymerized via complexation to the transition metal.

Also disclosed are polymer compositions. Generally, the disclosed polymer composition comprises a base polymer; an amide compound of Formula I-VI present in an amount of from about 0.10 to about 10 weight percent of the composition; and optionally, a transition metal in a positive oxidation state, the metal present in an amount of from about 10 ppm to about 400 ppm.

Generally, the amide compound is present in the composition in an amount of from 0.1 to about 10 weight percent. In one aspect, the amide compound is present in the composition in an amount of from 1 to about 10 weight percent. In a further aspect, the amide compound is present in the composition in an amount of from 1 to about 5 weight percent. In a further aspect, the amide compound is present in the composition in an amount of from 1 to about 3 weight percent.

A variety of different polymers can be used as the base polymer. The disclosed compositions enable oxygen scavenging, and thus the base polymer generally includes those polymers that can be subject to oxidation. For example, polymers that exhibit at least some oxygen permeability are useful with the disclosed compositions, at least inasmuch as the disclosed compositions can reduce the oxidative damage to the polymer.

The base polymer can be a polymer commonly used in packaging materials including polyethylene, such as low density polyethylene, very low density polyethylene, ultra-low density polyethylene, high density polyethylene, and linear low density polyethylene; polyesters such as (PET), (PEN) and their copolymers such as PET/IP; polyvinyl chloride (PVC); polyvinylidene chloride (PVDC); and ethylene copolymers such as ethylene/vinyl acetate copolymer, ethylene/alkyl (meth)acrylate copolymers, ethylene/(meth)acrylic acid copolymers, and ionomers. Blends of different base polymers also can be used.

In a further aspect, the base polymer can include one or more polymers approved by the U.S. Food and Drug Administration (FDA). Examples include polyethylene terephthalate, polypropylene, and polyethylene.

In a further aspect, the base polymer comprises a polyester polymer or copolymer. Preferred polyesters include polymers of phthalic acids, such as polyethylene terephthalate (PET), or a copolymer thereof. PET, for example, can be made from terephthalic acid and ethylene glycol. PET can also be made using dimethyl terephthalate and ethylene glycol. Preferred copolymers of phthalic acids include copolymers of a phthalic acid and one or more hydroxylated organic compounds. Examples of suitable hydroxylated organic compounds include 1,4-cyclohexandedimethanol, 1,2-propanediol, 1,4-butanediol, 2,2-dimethyl-1,3-propanediol, 2-methyl-1,3-propanediol (2 MPDO), 1,6-hexanediol, 1,2-cyclohexanediol, 1,4-cyclohexanediol, 1,2-cyclohexanedimethanol, 1,3-cyclohexanedimethanol, and diols containing one or more oxygen atoms in the chain, e.g., diethylene glycol, triethylene glycol, dipropylene glycol, tripropylene glycol, or mixtures of these, and the like.

In a still further aspect, the base polymer includes a polyethylene terephthalate homopolymer and copolymer modified with one or more polycarboxylic acid modifiers in a cumulative amount of less than about 15 mole %, or about 10 mole % or less, or about 8 mole % or less, or one or more hydroxyl compound modifiers in an amount of less than about 60 mol %, or less than about 50 mole %, or less than about 40 mole %, or less than about 15 mole %, or about 10 mole % or less, or about 8 mole % or less and polyethylene naphthalate homopolymers and copolymers modified with a cumulative amount of less than about 15 mole %, or about 10 mole % or less, or about 8 mole % or less, of one or more polycarboxylic acid modifiers or modified with less than about 60 mol %, or less than about 50 mole %, or less than about 40 mole %, or less than about 15 mole %, or about 10 mole % or less, or about 8 mole % or less of one or more hydroxyl compound modifiers, and blends thereof. In some aspects, the base polymer comprises at least 90 mole %, 92 mole %, or 94 mole % ethylene terephthalate repeat units based on the moles of all repeat units in the polyester polymers.

Polyesters such as PET can be prepared by polymerization procedures known in the art sufficient to effect esterification and polycondensation. Polyester melt phase manufacturing processes include direct condensation of a dicarboxylic acid with a diol, optionally in the presence of one or more esterification catalysts, in the esterification zone, followed by polycondensation in the prepolymer and finishing zones in the presence of a polycondensation catalyst; or ester exchange usually in the presence of a transesterification catalyst in the ester exchange zone, followed by prepolymerization and polymerization in the presence of a polycondensation catalyst.

As briefly discussed above, the composition can optionally comprise a transition metal in a positive oxidation state. The transition metal enhances the oxygen scavenging properties of the amide compound. Amounts of transition metal in the composition can be greater than zero and can be up to 5000 ppm. Generally, the transition metal will be present in an amount of from about 10 ppm to about 400 ppm. In one aspect, about 200 ppm of the transition metal is present. In a further aspect, about 250 ppm of the transition metal is present. In wall applications (as opposed to master batch applications where more transition metal is used), it can be preferred to keep the level of metal below 300, more preferably 250 ppm. In a further aspect, the transition metal is present from 30 to 150 ppm. In a further aspect, about 50 ppm of the transition metal is present. In a further aspect, about 100 ppm of the transition metal is present. In a further aspect, about 150 ppm of the transition metal is present.

In one aspect, the transition metal can be a transition metal from the first, second, or third transition series of the Periodic Table. The metal can be Rh, Ru, or one of the elements in the series of Sc to Zn (e.g., Sc, Ti, V, Cr, Mn, Fe, Co, Ni, Cu, and Zn). In one aspect, the transition metal is cobalt. Cobalt can be used in +2 or +3 oxidation states. In some aspects, it is preferred to use cobalt in the +2 oxidation state. In a further aspect, the transition metal is rhodium. For example, rhodium in the +2 oxidation state can be used. The transition metal can also be a positive oxidation form of zinc.

The transition metal can be present as a salt. The cation of the salt can be the transition metal in a positive oxidation state. A variety of anions can stabilize the positively charged transition metal. Suitable anions for the salts include, but are not limited to, chloride, acetate, oleate, stearate, palmitate, 2-ethylhexanoate, carboxylates, such as neodecanoates, octanoates, acetates, lactates, naphthalates, malates, stearates, acetylacetonates, linoleates, oleates, palmitates, 2-ethylhexanoates, or ethylene glycolates; or as their oxides, borates, carbonates, dioxides, hydroxides, nitrates, phosphates, sulfates, or silicates, among others. Representative transition metal salts include cobalt (II) 2-ethylhexanoate, cobalt oleate, and cobalt (II) neodecanoate. The transition metal salt also can be an ionomer, in which case a polymeric counter ion can be present.

In one aspect, the composition can comprise a colorant in a visually effective amount. A visually effective amount refers to an amount of colorant that results in the composition or an article made therefrom appear colored to the naked eye. A composition comprising a visually effective amount of colorant can refer to a composition having at least 0.01% by weight colorant. In a further aspect, the composition can comprise at least 0.25% by weight colorant. In a still further aspect, the composition can comprise at least 0.5% by weight colorant. The compositions can also comprise up to or even exceed about 3% by weight colorant.

A visually effective amount can be determined, for example, by performing a spectrophotometric scan of the composition or article using a wavelength range from 400 to 700 nm (visible region). Specific colors can be characterized according to their spectral pattern. Every color also has its own characteristic L (lightness gradation), a (red to green) and b (yellow to blue) numbers, which can be used to characterize the compositions and articles.

The colorant can be a variety of pigments and dyes, many of which are commercially available. Examples of colorants include without limitation COLORMATRIX Dark Amber, product code: 189-10034-6, COLORMATRIX Dead Leaf Green, product codes: 284-2801-3 and 84-2801-1, AMERICHEM amber, product code: 59108-CD1, Champaigne green, and COLORMATRIX amber, product code: 189-10100-1.

The composition can include other components such as fillers, crystallization aids, impact modifiers, surface lubricants, denesting agents, stabilizers, ultraviolet light absorbing agents, metal deactivators, nucleating agents such as polyethylene and polypropylene, phosphate stabilizers and dyestuffs. Typically, the total quantity of such components will be less than about 10% by weight of the composition. In some embodiments, the amount of these optional components is less than about 5% by weight of the composition.

The composition can comprise a reheat additive. Reheat additives are commonly used in the manufacture of polyester polymer compositions used to make stretch blow molded bottles because the preforms made from the composition must be reheated prior to entering the mold for stretch blowing into a bottle. Any conventional reheat additive can be used, such as various forms of black particles, e.g., carbon black, activated carbon, black iron oxide, glassy carbon, silicon carbide, gray particles such as antimony, and other reheat additives such as silicas, red iron oxide, and the like.

The composition can also comprise an impact modifier. Examples of typical impact modifiers useful in the composition include ethylene/acrylate/glycidyl terpolymers and ethylene/acrylate copolymers in which the acrylate is a methyl or ethyl acrylate or methyl or ethyl methacrylate or the corresponding butyl acrylates, styrene based block copolymers, and various acrylic core/shell type impact modifiers. The impact modifiers can be used in conventional amounts from about 0.1 to about 25 weight percent of the overall composition and, in some aspects, in amounts from about 0.1 to about 10 weight percent of the composition.

In many applications, not only are the packaging contents sensitive to the ingress of oxygen, but the contents may also be affected by UV light. Fruit juices and pharmaceuticals are two examples of such contents. Accordingly, in some aspects, it is desirable to incorporate into the composition a UV absorbing compound in an amount effective to protect the packaged contents.

The composition or an article made therefrom can have an Oxygen Transmission Rate (OTR) of less than about 0.1 (units of cc/pkg/day or 1-5 cc-mm/m²-day-atm) under standard conditions. In a further aspect, the OTR can be less than 0.03, less than 0.01, less than 0.005, or less than 0.001. The OTR is a measure of how well the amide compound functions at scavenging oxygen that permeates the composition or article.

When OTR is expressed for a given composition or article, the units "cc/package/day" ("cc/pkg/day") are typically employed. The term package refers to a barrier between an atmosphere of relatively lower oxygen content and an atmosphere of relatively higher oxygen content. Typical barriers (e.g., packages) include bottles, thermoformed containers, and films (e.g., shrink wrap).

Oxygen Transmission Rate (oxygen permeation) can be measured, for example, as described in U.S. Pat. No. 5,021,515. A material of area A can be exposed to a partial pressure p of oxygen on the one side and to an essentially zero partial pressure of oxygen on the other side. The quantity of oxygen emerging on the latter side is measured and expressed as a volume rate dV/dt, the volume being converted to some standard condition of temperature and pressure. After a certain time of exposure (usually a period of a few days) dV/dt is generally found to stabilize, and a $P_W$ value can be calculated from equation below:

$$dV/dt = P_W A p \quad (1)$$

$P_W$ refers to the permeance of the wall. (Analogy with magnetic permeance and electrical conductance would suggest that $P_W$ should be described as "permeance per unit area", but we are following the nomenclature in Encyclopaedia of Polymer Science and Technology, Vol. 2, Wiley Interscience, 1985, page 178.) The standard conditions for expressing dV/dt are 0° C. and 1 atm (1 atm=101 325 Nm⁻²). If the thickness of the area of wall is substantially constant over the area A with value T and the wall is uniform through the thickness (i.e., the wall is not a laminated or coated one) then the permeability of the material in the direction normal to the wall is calculated from the equation below.

$$dV/dt = P_M A p / T \quad (2)$$

For non-scavenging materials, $P_W$ and $P_M$ are to a reasonable approximation independent of t and p, and $P_M$ of T although they are often appreciably dependent on other conditions of the measurement such as the humidity of the atmosphere on the oxygen-rich side and the temperature of the measurement.

For oxygen-scavenging walls, $P_W$ and $P_M$ are functions of t because the concentrations and activity of scavenger vary with time (particularly as the scavenger is consumed). This typically does not prevent measurement of $P_W$ and $P_M$ reasonably accurately as a function of time, because the changes in dV/dt are relatively gradual once the normal initial equilibration period of a few days is over. After a few days' exposure to the measurement conditions, however, a non-scavenging material typically achieves a steady state in which dV/dt is equal to the rate of oxygen ingress to the wall, while a scavenging material achieves an (almost) steady state in which dV/dt is considerably less than the rate of oxygen ingress to the material. This being the case, it is likely that $P_W$ calculated from (1) is a function of p as well as of t and that $P_M$ in (2) is a function of p and T as well as of t. $P_W$ and $P_M$ for scavenging materials are, strictly speaking, not true permeances and permeabilities at all (since permeation and scavenging are occurring simultaneously) but, rather, apparent ones.

Values of $P_W$ and $P_M$ (except where stated otherwise) are to be understood to refer to conditions in which p=0.21 atm, the relative humidity on the oxygen-rich side of the wall is 50%, the temperature is 23° C. and (in the case of $P_M$ values) the thickness of the material of about 0.45 mm. Conditions close to the first three of these, at least, are conventional in the packaging industry.

For example, OTR can be measured for bottles, for example, by controlling the atmosphere on both sides of a sample of bottles and measuring the rate of oxygen permeation over time. Typically, the bottles are mounted on a plate such that there are two ports for gas inlet and outlet. The interior of the bottles is separated from the exterior by an air tight seal. After sealing, the interior of the bottle is flushed with $N_2$ gas (or $N_2+H_2$ mixture) to remove any oxygen present before mounting on plate. The bottle is then placed in a controlled environmental chamber (maintained at 23° C. and 50% RH) such that the exterior of the bottle is at standard atmosphere with ~21% oxygen. The interior of the bottle is continuously flushed with $N_2$ (or $N_2+H_2$) at a known gas flow rate. The outlet of the flushed gases contains oxygen permeating through the bottle wall. This flushed gas from the bottle interior is passed over a sensor that is calibrated to measure oxygen content of the flushed gas. Such measurements of oxygen content are made continuously over time until a steady state is reached. This steady state value is typically reported as Oxygen Transmission Rate (OTR) for that bottle in the units of cc/package/day. A preferred OTR for PET bottles is less than 0.1 cc/package/day; more preferred is less than 0.01 cc/package/day; most preferred for PET bottles is less than 0.001 cc/package/day over the shelf life of the packaged product.

In one aspect, a disclosed composition has an OTR of less than that of an otherwise identical composition in the absence of the amide compound and the transition metal. In further aspects, a disclosed composition has an OTR of less than about 75%, less than about 50%, less than about 25%, less than about 20%, less than about 10%, less than about 5%, or less than about 1% of an otherwise identical composition in the absence of the amide compound and the transition metal.

Various methods exist for making the composition. In one aspect, the composition can be made by mixing the base polymer with the amide compound and optionally the transition metal. In some aspects, some or part of the transition metal may already be present in the base polymer prior to mixing, for example if the transition metal is used as a catalyst for making the base polymer. In some aspects, the base polymer, the oxidizable organic component and the transition metal are mixed by tumbling in a hopper. Other optional ingredients can be added during this mixing process or added to the mixture after the aforementioned mixing or to an individual component prior to the aforementioned mixing step.

When melt processing is desired for the composition, the composition can also be made by adding each ingredient separately and mixing the ingredients just prior to melt processing the composition to form an article. In some embodiments, the mixing can be just prior to the melt process zone. In other embodiments, one or more ingredients can be pre-mixed in a separate step prior to bringing all of the ingredients together.

In some aspects, the transition metal can be added neat or in a carrier (such as a liquid or wax) to an extruder or other device for making the article, or the metal can be present in a concentrate or carrier with the amide compound, in a concentrate or carrier with the base polymer, or in a concentrate or carrier with a base polymer/amide compound blend. It is desirable that the addition of the transition metal does not substantially increase the intrinsic viscosity of the melt in the melt processing zone. Thus, transition metal or metals can be added in two or more stages, such as once during the melt phase for the production of the base polymer and again once more to the melting zone for making the article.

The melt blend of base polymer, amide compound, and transition metal catalyst can also be prepared by adding the components at the throat of an injection molding machine that: (i) produces a preform that can be stretch blow molded into the shape of the container, (ii) produces a film that can be oriented into a packaging film, (iii) produces a sheet that can be thermoformed into a food tray, or (iv) produces an injection molded container. The mixing section of the extruder should be of a design to produce a homogeneous blend. Such process steps work well for forming carbonated soft drink, water or beer bottles, packaging films and thermoformed trays. The present invention can be employed in any of the conventional known processes for producing a polymeric container, film, tray, or other article that would benefit from oxygen scavenging.

Various articles can be prepared from the disclosed compositions. Thus, the articles prepared from the compositions will also have the composition present in the article. Suitable articles include vessels and films, such as flexible sheet films, flexible bags, pouches, semi-rigid and rigid containers such as bottles (e.g. PET bottles) or metal cans, or combinations thereof. Typical flexible films and bags include those used to package various food items and can be made up of one or a multiplicity of layers to form the overall film or bag-like packaging material. The composition of the present invention can be used in one, some or all of the layers of such packaging material.

Specific articles include preforms, containers and films for packaging of food, beverages, cosmetics, pharmaceuticals, and personal care products where a high oxygen barrier is needed. Examples of beverage containers are bottles for holding water and carbonated soft drinks, and the invention is particularly useful in bottle applications containing juices, sport drinks, beer or any other beverage where oxygen detrimentally affects the flavor, fragrance, performance (e.g., vitamin degradation), or color of the drink. The compositions are also particularly useful as a sheet for thermoforming into rigid packages and films for flexible structures. Rigid packages include food trays and lids. Examples of food tray applications include dual ovenable food trays, or cold storage food trays, both in the base container and in the lidding (whether a thermoformed lid or a film), where the freshness of the food contents can decay with the ingress of oxygen. The compositions can also be used in the manufacture of cosmetic containers and containers for pharmaceuticals or medical devices.

Other suitable articles include rigid or semi-rigid articles including plastic, such as those utilized for juices, soft drinks, as well as thermoformed trays or cup normally having thickness in the range of from 100 to 1000 micrometers. The walls of such articles can comprise single or multiple layers of materials. The article can also take the form of a bottle or can, or a crown, cap, crown or cap liner, plastisol or gasket. The composition of the present invention can be used as an integral layer or portion of, or as an external or internal coating or liner of, the formed semi-rigid or rigid packaging article. As a liner, the composition can be extruded as a film along with the rigid article itself, e.g., by coextrusion, extrusion coating, or an extrusion lamination process, so as to form the liner in situ during article production; or alternatively can be adhered by heat and/or pressure, by adhesive, or by any other suitable method.

When the compositions are used in a wall or as a layer of a wall, the permeability of the composition for oxygen is advantageously not more than about 3.0, or about 1.7, or about 0.7, or about 0.2, or about 0.03 $cm^3$-mm/($m^2$-atm-day). In some aspects, the permeability of the composition is not more than about three-quarters of that in the absence of the amide compound. In some aspects, the permeability is not more than about one half, one-tenth in certain embodiments, one twenty-fifth in other embodiments, and not more than one-hundredth of that in the absence of the amide compound.

Although it can be preferable from the standpoint of packaging convenience and/or scavenging effectiveness to employ the present invention as an integral or discrete part of the packaging wall, the invention can also be used as a non-integral component of a packaging article such as, for example, a bottle cap liner, adhesive or non-adhesive sheet insert, sealant, sachet, fibrous mat insert or the like.

Besides articles applicable for packaging food and beverage, articles for packaging other oxygen-sensitive products can also benefit from the present invention. Such products would include pharmaceuticals, oxygen sensitive medical products, corrodible metals or products, electronic devices and the like.

In a further aspect, the composition can be used as a master batch for blending with a polymer or a polymer containing component. In such compositions, the concentration of the amide compound and the transition metal will be high enough to allow for the final blended product to have suitable amounts of these components. The master batch can also contain an amount of the base polymer with which the master batch is blended.

Oxygen permeability of an article can be maintained for a longer period of time by storing the article in a sealed container or under an inert atmosphere such as nitrogen prior to use with oxygen sensitive materials.

The articles can be made by various methods known in the art. Generally, the articles are prepared by melt processing methods (i.e., a melt of the composition). Such processes generally include injection molding, stretch blow molding, extrusion, thermoforming, extrusion blow molding, and (specifically for multilayer structures) co-extrusion and lamination using adhesive tie layers. Orientation, e.g., by stretch blow molding, of the polymer can be used with phthalate polyesters because of the known mechanical advantages that result.

The melt processing zone for making the article can be operated under customary conditions effective for making the intended articles, such as preforms, bottles, trays, and other articles mentioned above. In one aspect, such conditions are effective to process the melt without substantially increasing the intrinsic viscosity of the melt and which are ineffective at promoting transesterification reactions. In some preferred aspects, suitable operating conditions effective to establish a physical blend of the base polymer, oxidizable organic component, and transition metal are temperatures in the melt processing zone within a range of about 250° C. to about 300° C. at a total cycle time of less than about 6 minutes, and typically without the application of vacuum and under a positive pressure ranging from about 0 psig (pound-force per square inch gauge) to about 900 psig. In some embodiments, the residence time of the melt on the screw can range from about 1 to about 4 minutes.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Synthesis of
1,3,5-Tris(phthalimidinomethyl)benzene

A mixture of 61.1 g (459 mmol) of phthalimidine, 42.9 g (120 mmol) of 1,3,5-tris(bromomethyl)benzene and 177.1 g (544 mmol) of $Cs_2CO_3$ in 1 L of $CH_3CN$ was refluxed for 19 hours. After cooling to room temperature, the reaction mixture was partitioned between 1 L of EtOAc and 1 L of deionized water and the phases were separated. The organic phase was washed with 802g of brine and dried over 203 g of anhydrous $Na_2SO_4$. The liquid was decanted from the drying agent and the drying agent was slurried in 500 ml of $CH_2Cl_2$ to try to dissolve some insoluble brown solid that remained. The combined organic phases were concentrated in vacuo to yield 74.1 g of orange solid. TLC (EtOAc) showed this material to be a mixture of the desired product and starting phthalimidine.

The crude material was dissolved in 200 ml of $CH_2Cl_2$ @ 35° C. Half of this was chromatographed over 1163 g of silica gel (70-230 mesh), eluting with EtOAc. After a forerun of 1.3 L, 70×250 ml fractions were cut. Pure product fractions were pooled and concentrated in vacuo. The second half of the crude solution was chromatographed similarly and product fractions combined with those from the first run. The yield, after collection and drying in vacuo to constant weight, was 8.6 g.

The second column was washed exhaustively with EtOAc in the suspicion that the product, with limited solubility in EtOAc, had crystallized on the column and was being slowly eluted off. Washing the column with 4.5 L of EtOAc gave another 4.0 g of product.

The reaction scheme is depicted below:

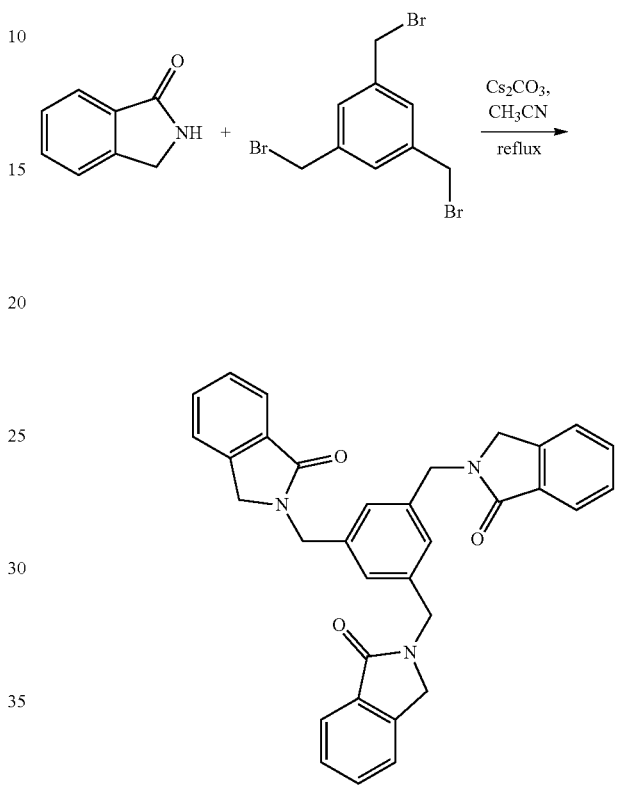

Example 2

The compound, DCX-600 prepared in Example 1 {1,3,5-Tris(phthalimidinomethyl)benzene OR [1,3,5-phenylenetris (methylene)]tris-[2,3-dihydro-1H-Isoindol-1-one]} was mixed at 1.4 wt % with hot, dry PET resin (Vitiva™ from Eastman Chemical Company) and 80 ppm Cobalt catalyst (added as a PET based masterbatch). This mixture was fed into BOY 22S injection molding machine to mold plaques. To compare the $O_2$ scavenging performance of DCX-600, plaques made with DC-300 (LDR=1.4 wt %) were also molded at the same time, under similar processing conditions. These plaques were ground up and analyzed for $O_2$ scavenging performance using Oxysense™. FIG. 1 shows the Oxysense data for compound DCX-600 as a function of time. As seen from FIG. 1, plaques made using DCX-600 compound in PET scavenged oxygen at a rate similar to DC-300 at 75 C.

Example 3

The compound 2-benzyl-1-isoindolinone (DCX-300-1) was prepared by reacting benzyl amine with phthalide (2-benzofuran-1(3H)-one. The chemical structure of 2-benzyl-1-isoindolinone is shown below:

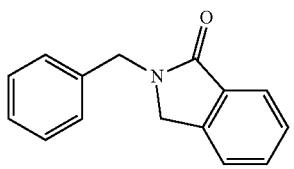 [SMILES: O=C1c2ccccc2CN1Cc1ccccc1]

Figure 2:
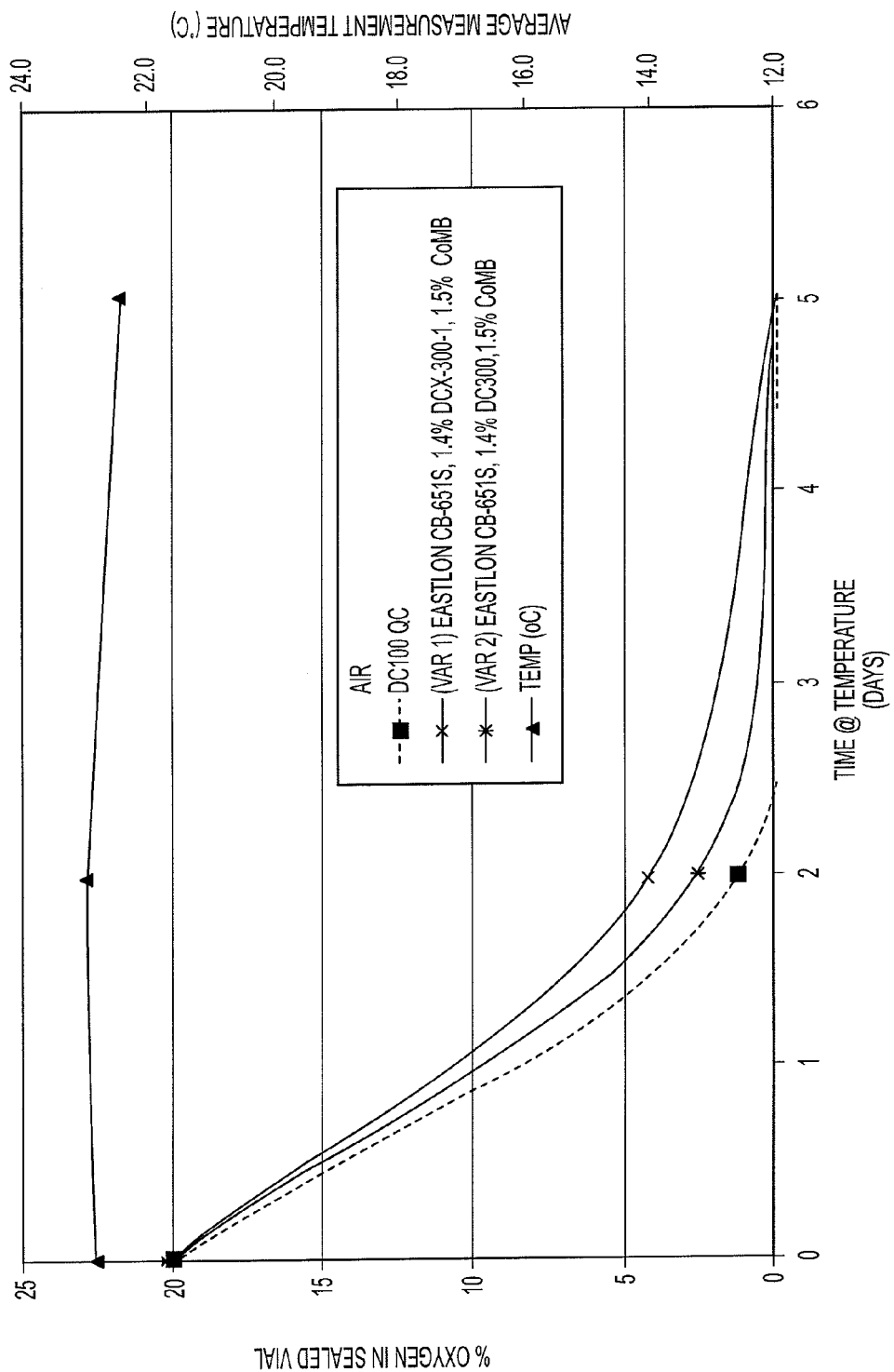
FIG. 2 shows Oxysense™ $O_2$ scavenging data for DCX-300-1 (di-functional scavenger) and DC-300 (tetra-functional scavenger) containing plaques, as described in Example 3.

1.4 weight % of this compound DCX-300-1 (lot number LP 081710, prepared by Cymer LLC, Decatur, Tenn.) was mixed with dried Eastlon CB-651S (lot number 0104896, manufactured by Far Eastern Textiles) resin and 80 ppm cobalt catalyst (added as a solid masterbatch of Cobalt Neodecanoate in PET). The PET resin was dried in a Piovan dryer at 170 C for 4 hours before being used for mixing. The mixture was fed into the BOY 22 S injection molding machine to mold plaques. The BOY 22 S injection molder barrel temperatures during injection molding was ~275° C. for both heating zones, the injection pressure was ~700 psi, nozzle heater and sprue heater temperatures were ~280° C. The mold was water cooled. The plaques were tested for oxygen scavenging using Oxysense™. The Oxysense data is shown in FIG. 2. As seen from FIG. 2, the di-functional $O_2$ scavenger (DCX-300-1) scavenges $O_2$ at a rate similar to that for Constar International's DC-300 oxygen scavenger (tetra-functional O2 scavenger)

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A melt blended polymer composition comprising:
   a. a base polymer;
   b. at least one compound having a structure of Formula I-VI present in an amount of from about 0.10 to about 10 weight percent of the composition; and
   c. a transition metal in a positive oxidation state, the metal present in an amount of from about 10 ppm to about 400 ppm;

wherein Formula I and Formula II are compounds having the following structures:

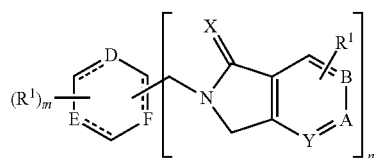
(I)

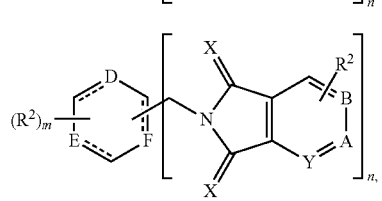
(II)

wherein the symbol --- when used in conjunction with a bond line represents a single or a double bond;

wherein n is 3, 4, 5, or 6;
wherein m is an integer from 0 to 6-n;
wherein each X is independently selected from the group consisting of O, S, and NH;
wherein each Y, each A, and each B are independently selected from the group consisting of N, $CR^1$, and $CR^2$;
wherein D, E, and F are independently selected from the group consisting of CH, N, O, and S; and
wherein each $R^1$ and each $R^2$ is independently selected from the group consisting of H, alkyl, aryl, electron withdrawing groups, electron releasing groups, and a transition metal;

Formula III and Formula IV are compounds having the following structures:

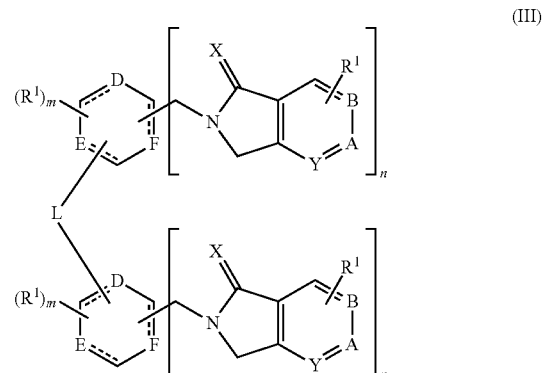
(III)

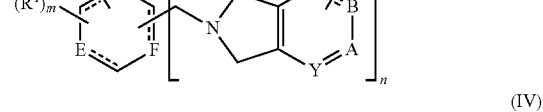

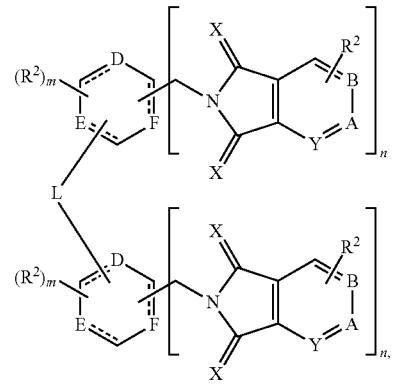
(IV)

wherein the symbol --- when used in conjunction with a bond line represents a single or a double bond;
wherein each n is independently 1-5;
wherein m is an integer from 0 to 5-n;
wherein each X is independently selected from the group consisting of O, S, and NH;
wherein each Y, each A, and each B are independently selected from the group consisting of N, $CR^1$ and $CR^2$;
wherein D, E, and F are independently selected from the group consisting of CH, N, O, and S;
wherein each $R^1$ and each $R^2$ is independently selected from the group consisting of H, alkyl, aryl, electron withdrawing groups, electron releasing groups, and a transition metal; and
wherein L is a divalent linking group selected from C2-C12 aliphatic or cyclic ether, C2-C12 aliphatic or cyclic amide, C6 to C12 aromatic amide, C2-C12 aliphatic or cyclic amine, C6-C12 aromatic amine, C2-C12 aliphatic or cyclic ester and C6 to C12 aromatic ester;

and Formula V and VI are compounds having the following structures:

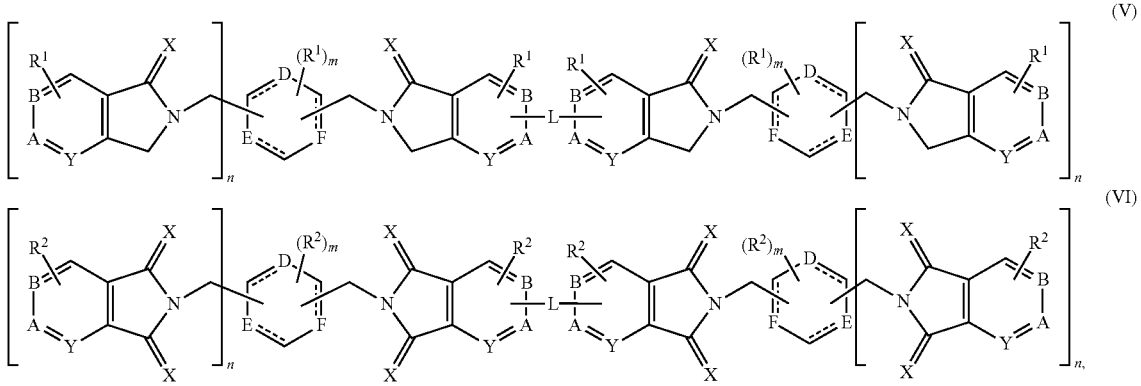

wherein the symbol --- when used in conjunction with a bond line represents a single or a double bond;
wherein each n is independently 0-5;
wherein m in is an integer from 0 to 5-n;
wherein each X is independently selected from the group consisting of O, S, and NH;
wherein each Y, each A, and each B are independently selected from the group consisting of N, $CR^1$, and $CR^2$;
wherein D, E, and F are independently selected from the groups consisting of CH, N, O, and S;
wherein each $R^1$ and each $R^2$ is independently selected from the group consisting of H, alkyl, aryl, electron withdrawing groups, electron releasing groups, and a transition metal; and
wherein L is a divalent linking group selected from C2-C12 aliphatic or cyclic ether, C2-C12 aliphatic or cyclic amide, C6 to C12 aromatic amide, C2-C12 aliphatic or cyclic amine, C6-C12 aromatic amine, C2-C12 aliphatic or cyclic ester and C6 to C12 aromatic ester.

2. The composition of claim 1, wherein the composition has an OTR of less than about 0.1 cc/package/day.

3. The composition of claim 1, further comprising a visually effective amount of colorant.

4. The composition of claim 1, wherein the transition metal is cobalt.

5. The composition of claim 4, wherein the transition metal further comprises zinc.

6. The composition of claim 1, wherein the concentration of transition metal is 30 to 150 ppm.

7. The composition of claim 1, wherein the base polymer comprises a polyester polymer or copolymer.

8. The composition of claim 1, wherein the base polymer comprises polyethylene terephthalate or copolymer thereof.

9. The composition of claim 1, wherein the compound having a structure of Formula I-VI is present in an amount of about 1 to about 10 weight percent based on the weight of the composition.

10. The composition of claim 1, wherein the compound having a structure of Formula I-VI is present in an amount of about 1 to about 5 weight percent based on the weight of the composition.

11. The composition of claim 1, wherein the compound having a structure of Formula I-VI is present in an amount of about 1 to about 3 weight percent based on the weight of the composition.

12. An article comprising a composition of a base polymer; at least one compound having a structure of Formula I-VI present in an amount of from about 0.10 to about 10 weight percent of the composition; and a transition metal in a positive oxidation state, the metal present in an amount of from about 10 ppm to about 400 ppm;
wherein Formula I and Formula II are compounds having the following structures:

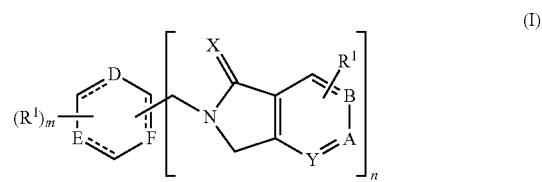

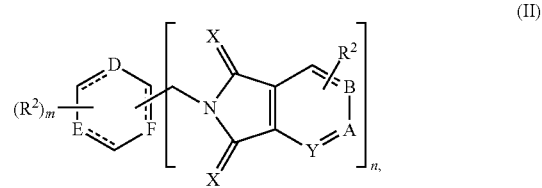

wherein the symbol --- when used in conjunction with a bond line represents a single or a double bond;
wherein n is 3, 4, 5, or 6;
wherein m is an integer from 0 to 6-n;
wherein: each X is independently selected from the group consisting of O, S, and NH;
wherein each Y, each A, and each B are independently selected from the group consisting of N, $CR^1$, and $CR^2$;
wherein D, E, and F are independently selected from the group consisting of CH, N, O, and S; and
wherein each $R^1$ and each $R^2$ is independently selected from the group consisting of H, alkyl, aryl, electron withdrawing groups, electron releasing groups, and a transition metal;
Formula III and Formula IV are compounds having the following structures:

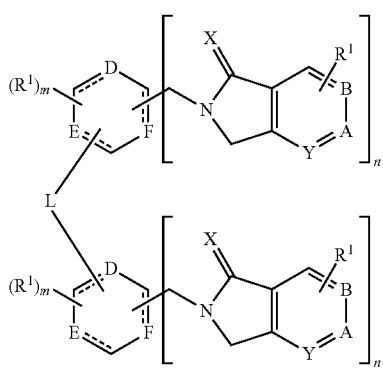

(III)

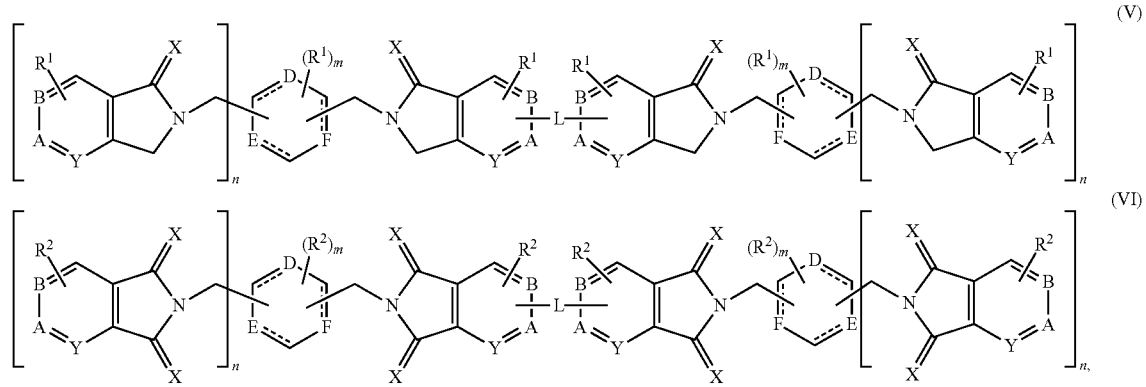

(V)

(VI)

-continued

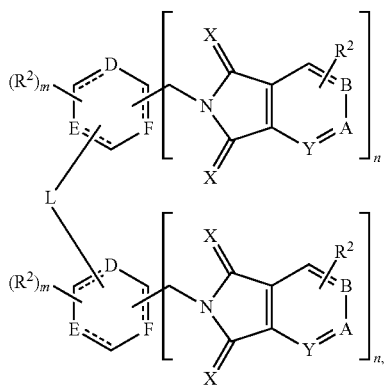

(IV)

wherein the symbol --- when used in conjunction with a bond line represents a single or a double bond;

wherein each n is independently 1-5;

wherein m in is an integer from 0 to 5-n;

wherein each X is independently selected from the group consisting of O, S, and NH;

wherein each Y, each A, and each B are independently; selected from the group consisting of N, $CR^1$, and $CR^2$;

wherein D, E, and F are independently selected from the group consisting of CH, N, O, and S;

wherein each $R^1$ and each $R^2$ is independently selected from the group consisting of H, alkyl, aryl, electron withdrawing groups, electron releasing groups, and a transition metal; and wherein L is a divalent linking group selected from C2-C12 aliphatic or cyclic ether, C2-C12 aliphatic or cyclic amide, C6 to C12 aromatic amide, C2-C12 aliphatic or cyclic amine, C6-C12 aromatic amine, C2-C12 aliphatic or cyclic ester and C6 to C12 aromatic ester;

and Formula V and VI are compounds having the following structures:

wherein the symbol --- when used in conjunction with a bond line represents a single or a double bond:

wherein each n is independently 0-5;

wherein m is an integer from 0 to 5-n;

wherein each X is independently selected from the group consisting of O, S, and NH;

wherein each Y, each A, and each B are independently selected from the group consisting of N, $CR^1$, and $CR^2$;

wherein D, E, and F are independently selected from die group consisting of CH, N, O, and S;

wherein each $R^1$ and each $R^2$ is independently selected from the group consisting of H, alkyl, aryl, electron withdrawing groups, electron releasing groups, and a transition metal; and wherein L is a divalent linking group selected from C2-C12 aliphatic or cyclic ether, C2-C12 aliphatic or cyclic amide, C6 to C12 aromatic amide, C2-C12 aliphatic or cyclic amine, C6-C12 aromatic amine, C2-C12 aliphatic or cyclic ester and C6 to C12 aromatic ester.

13. The article of claim 12, dimensioned as a vessel.

14. The article of claim 12, dimensioned as a film.

* * * * *